(12) United States Patent
Price et al.

(10) Patent No.: US 7,814,630 B2
(45) Date of Patent: Oct. 19, 2010

(54) APPARATUS AND METHOD FOR SWAGING NEEDLES

(75) Inventors: John J. Price, Seneca, SC (US); Jerry W. Stametz, Cornelia, GA (US); Kenneth R. Barsch, San Angelo, TX (US)

(73) Assignee: Ethicon, Inc., Somerville, NJ (US)

( * ) Notice: Subject to any disclaimer, the term of this patent is extended or adjusted under 35 U.S.C. 154(b) by 615 days.

(21) Appl. No.: 11/601,077

(22) Filed: Nov. 17, 2006

(65) Prior Publication Data
US 2008/0119876 A1  May 22, 2008

(51) Int. Cl.
B21J 7/16 (2006.01)
(52) U.S. Cl. .................... 29/243.58; 29/243.57; 72/220; 606/144
(58) Field of Classification Search ............... 29/243.58, 29/243.57, 243.5, 281.1; 72/220, 214; 606/144
See application file for complete search history.

(56) References Cited

U.S. PATENT DOCUMENTS

| | | | |
|---|---|---|---|
| 1,558,037 A | 10/1925 | Morton | |
| 1,665,216 A | 4/1928 | Morton | |
| 2,008,227 A | 7/1935 | Reilly | |
| 2,131,766 A | 10/1938 | Temple | |
| 2,621,385 A | 12/1952 | Gilmore | |
| 2,741,752 A | 4/1956 | Edwards | |
| 2,802,468 A | 8/1957 | Everett et al. | |
| 2,910,983 A | 11/1959 | Everett | |
| 2,928,395 A | 3/1960 | Forbes et al. | |
| 3,394,704 A | 7/1968 | Dery | |
| 3,799,159 A | 3/1974 | Beroff et al. | |

(Continued)

FOREIGN PATENT DOCUMENTS

AU   B-58368/80   8/1980

(Continued)

OTHER PUBLICATIONS

International Patent Application No. PCT/US2009/066772, filed Apr. 12, 2009, entitled: "Surgical Needle Swage Tool".

(Continued)

*Primary Examiner*—Lee D Wilson

(57) ABSTRACT

A method and apparatus for making armed sutures has a pair of opposed die assemblies that may be driven by actuating surfaces of a swaging machine to hold and swage a needle on a suture. The dies grip and confine the needle in the area of the suture receptacle. A pair of opposed swaging elements with offset stakes insert through passageways in the dies and impinge on the captured needle making a plurality of indentations in the needle barrel and gripping the suture in the suture receptacle. The indentations are offset and aligned generally in alternating peak-to-valley relationship, causing the suture receptacle and the contained suture to assume a serpentine configuration. The stakes and the resulting indentations can be dimensioned to result in a converging suture receptacle, which exhibits increasing shear force being exerted on the suture with increasing depth into the suture receptacle. The apparatus and method permit reliable suture-needle attachment over a larger range of tolerances, such that a single die setup can be used on a plurality of needle and suture materials. The resulting product exhibits a serpentine suture/needle attachment interface with reliable attachment and smooth outer dimensions.

8 Claims, 9 Drawing Sheets

U.S. PATENT DOCUMENTS

| | | | |
|---|---|---|---|
| 3,890,975 A | 6/1975 | McGregor | |
| 3,910,282 A | 10/1975 | Messer et al. | |
| 3,924,630 A | 12/1975 | Walldorf | |
| 4,054,144 A | 10/1977 | Hoffman et al. | |
| 4,060,885 A | 12/1977 | Hoffman et al. | |
| 4,072,041 A | 2/1978 | Hoffman et al. | |
| 4,124,027 A | 11/1978 | Boss | |
| 4,127,133 A | 11/1978 | Martinez | |
| 4,182,341 A | 1/1980 | Perri | |
| 4,630,617 A | 12/1986 | Ritter et al. | |
| 4,799,484 A | 1/1989 | Smith et al. | |
| 4,832,025 A | 5/1989 | Coates | |
| 4,922,904 A | 5/1990 | Uetake et al. | |
| 5,000,912 A | 3/1991 | Bendel et al. | |
| 5,007,922 A | 4/1991 | Chen et al. | |
| 5,046,350 A | 9/1991 | Proto et al. | |
| 5,099,676 A | 3/1992 | Proto et al. | |
| 5,131,131 A | 7/1992 | Proto et al. | |
| 5,139,514 A | 8/1992 | Korthoff et al. | |
| 5,156,615 A | 10/1992 | Korthoff et al. | |
| 5,168,619 A * | 12/1992 | Proto et al. | 29/508 |
| 5,201,760 A | 4/1993 | West | |
| 5,207,701 A | 5/1993 | West | |
| 5,224,955 A | 7/1993 | West | |
| 5,259,846 A | 11/1993 | Granger et al. | |
| 5,268,014 A | 12/1993 | Miller et al. | |
| 5,350,373 A | 9/1994 | Colligan | |
| 5,383,902 A | 1/1995 | Carpentiere et al. | |
| 5,394,726 A | 3/1995 | Bogart et al. | |
| 5,403,345 A | 4/1995 | Spingler | |
| 5,438,746 A | 8/1995 | Demarest et al. | |
| 5,462,543 A | 10/1995 | Colligan | |
| 5,473,810 A | 12/1995 | Demarest et al. | |
| 5,487,212 A | 1/1996 | Demarest et al. | |
| 5,487,216 A | 1/1996 | Demarest et al. | |
| 5,487,308 A | 1/1996 | Demarest et al. | |
| 5,495,420 A | 2/1996 | Demarest et al. | |
| 5,500,991 A | 3/1996 | Demarest et al. | |
| 5,507,798 A | 4/1996 | Colligan et al. | |
| 5,568,746 A | 10/1996 | Colligan et al. | |
| 5,569,302 A | 10/1996 | Proto et al. | |
| 5,593,425 A | 1/1997 | Bonutti et al. | |
| 5,608,962 A | 3/1997 | Colligan et al. | |
| 5,651,843 A | 7/1997 | Bendel et al. | |
| 5,697,134 A * | 12/1997 | Spaulding et al. | 29/225 |
| 5,707,391 A | 1/1998 | Carpentieri | |
| 5,713,116 A * | 2/1998 | Nickerson et al. | 29/243.518 |
| 5,722,991 A * | 3/1998 | Colligan | 606/223 |
| 5,844,142 A | 12/1998 | Blanch et al. | |
| 5,891,164 A | 4/1999 | Dabir et al. | |
| 6,012,216 A | 1/2000 | Esteves et al. | |
| 6,031,018 A | 2/2000 | Scopelianos et al. | |
| 6,032,343 A | 3/2000 | Blanch et al. | |
| 6,056,771 A | 5/2000 | Proto | |
| 6,081,981 A | 7/2000 | Demarest et al. | |
| 6,163,948 A | 12/2000 | Esteves et al. | |
| 6,263,558 B1 | 7/2001 | Blanch et al. | |
| 6,322,582 B1 | 11/2001 | Richard et al. | |
| 6,360,415 B1 * | 3/2002 | Wada et al. | 29/283.5 |
| 6,877,352 B1 | 4/2005 | Schlereth | |
| 6,939,365 B1 | 9/2005 | Fogarty et al. | |
| 7,165,311 B2 * | 1/2007 | Schwar | 29/505 |
| 7,322,086 B2 | 1/2008 | Humpert et al. | 29/243.5 |
| 7,591,054 B2 * | 9/2009 | Baughman | 29/243.5 |
| 2005/0113869 A1 | 5/2005 | Price | |
| 2008/0119876 A1* | 5/2008 | Price et al. | 606/144 |
| 2008/0161850 A1 | 7/2008 | Weisenburgh et al. | |

FOREIGN PATENT DOCUMENTS

| | | |
|---|---|---|
| JP | 405154158 A | 6/1993 |
| JP | 2002034992 A | 2/2002 |

OTHER PUBLICATIONS

International Search Report and Written Opinion for PCT/US2009/066772, mailed Feb. 19, 2010.

Technical Data Sheet Product 4302, Locite Corporation, Rocky Hill, CT May 1998, pp. 1-2.

U.S. Appl. No. 12/330,702, filed Dec. 9, 2008, entitled "Surgical Needle Swage Tool".

* cited by examiner

APPARATUS AND METHOD FOR SWAGING NEEDLES

FIELD OF THE INVENTION

The present invention relates to apparatus and methods for attaching needles to sutures, such as for making armed sutures for surgical application, and more particularly, to methods of attaching surgical needles to sutures using a swaging process.

BACKGROUND OF THE INVENTION

Various methods for swaging needles to sutures are known. Given a needle of a desired gauge, composition and shape, a hole is formed in one end. The hole extends axially into the needle to constitute a suture receptacle and may be formed by mechanical or laser drilling. The term "needle" as used herein is intended to refer to a surgical needle, such that the term "needle" is intended to be a short form of the term "surgical needle" and is synonymous therewith. Typically, the end of the needle having the suture receptacle could be generally described as being in the form of a hollow cylinder, the diameter of the interior hollow of the cylinder being greater than the outside diameter of the suture to be attached to the needle, providing a clearance for insertion of the suture. To attach the suture, a free end of a suture is slidably, axially inserted into the suture receptacle (hole) in the needle and held in that position while a swage die impinges upon the outer peripheral surface of the needle receptacle (the outer surface of the cylinder), collapsing some or all of the cylinder radially inwardly, such that the interior dimensions of the suture receptacle are reduced at some portion thereof. The reduced interior dimensions of the needle receptacle grasp the inserted suture end via mechanical interference and by surface contact (friction). Generally, suture material has some degree of deformability/malleability, but there are limits to same, which, when exceeded, lead to suture material failure. Similarly, there are limits (albeit generally less problematic) to the malleability/deformability/elasticity of needle materials. In swaging, it is desirable to preserve a smooth and continuous exterior needle surface in the area of the suture receptacle. Out of round conditions or sharp edges produced by swaging can increase the drag that the needle experiences when passing through the tissue being sutured, injure the tissue and/or unnecessarily enlarge the hole in the tissue made by the needle as it is passes through the tissue during use. Manufacturing artifacts that protrude from the surface of the needle in the swaging area, (such as "fins") sometimes occur when the swaging is conducted by a pair of dies which abut one another in the compressed position of a swaging operation. Sharp edges transverse to the axial direction are also sometimes produced by swaging processes at the transition from the uncompressed to the compressed/deformed swaged area of the needle. One approach that has been utilized to provide good suture attachment and smooth outer surfaces in the swaged area is multiple hit swaging, wherein a needle is subjected to swaging of controlled depth, but distributed over a larger area, viz., around the circumference of the needle. To achieve this type of swaging, the needle is rotated (repositioned relative to the swaging dies between multiple swaging compressions. In this manner, multiple angularly offset swaging operations (hits) are performed to attach a single needle to a single suture. While this produces good results, the apparatus used is more complex and expensive than single hit swaging apparatus and the process takes longer. Yet another approach is to use confined stake swaging, wherein the suture receptacle end of a needle to be swaged is inserted between a pair of mating holding dies which, when compressed together, define a substantially cylindrical cavity that grips the needle securely, but does not deform the needle, i.e., the holding dies do not swage the needle. After being gripped by the holding dies, a suture is inserted into the suture receptacle in the needle. One or more elongated swaging elements with one or more staking points (stakes or nibs) slidably extend through the holding dies in mating channel(s) provided therein. When the swaging operation is conducted, the stake(s) are driven into the needle and deform the receptacle end of the constrained needle, such that the needle grips the suture. The holding dies insure that the outer periphery of the needle is supported to allow the stakes to deform the needle in a very localized area without otherwise deforming the receptacle end of the needle. Two adjacent stake swages may be employed to produce two adjacent, inwardly extending dimples/indentations that protrude into the needle receptacle area to capture the suture between the dimples and interior surface of the suture receptacle to grip the suture therebetween. The result is a double stake swaged needle with a pair of indentations but no protrusions, out of round areas or sharp ledges formed as a consequence of swaging.

While double stake swaging produces good results, the process requires a high degree of precision, in particular when used to swage needles to monofilament sutures and to sutures that are made from materials that are sensitive to being pinched off or clipped by the inwardly converging dimples. For example polypropylene is less deformable/malleable than other suture materials, e.g., nylon and tends to be clipped off when subjected to excessive pinching pressure/shear forces. Precision in the formation of the needle diameter, needle hole (and resultant wall thickness), suture diameter, and depth of penetration of the stake swage dies all must be closely controlled to prevent excessive shear force on the suture, while insuring adequate force to provide secure attachment. The precise setup will typically vary for each type of suture/needle combination, requiring reconfiguration of the swaging apparatus for each different product run. During production, testing is used to insure that adequate needle pull-off strength is achieved. Since insuring effective attachment without compromising suture integrity adds significantly to the cost of armed suture production, it remains an objective to make the process easier, more efficient and effective.

SUMMARY OF THE INVENTION

The problems and disadvantages associated with conventional armed sutures and the apparatus and techniques utilized to manufacture them are overcome by the present invention, which includes a swaging apparatus driven by a swaging machine with a pair of actuating surfaces that selectively converge to exert pressure and diverge to release pressure on the swaging apparatus for attaching a needle to a suture. The needle has a suture receptacle at one end for receiving the suture, which is retained therein by swaging. The swaging apparatus includes a die assembly with a needle aperture, which slideably accommodates the needle. The die assembly has a plurality of a swage passageways therein communicating with the needle aperture and extending through the die assembly at a plurality of radial orientations relative to the needle aperture. A plurality of swaging elements are insertable into corresponding ones of the plurality of swage passageways, each of the swaging elements having an end with at least one stake. At least one of the stakes on a first swaging element is longitudinally offset relative to the stakes on the remainder of the plurality of swaging elements.

A method in accordance with the present invention for attaching a needle having a suture receptacle at one end to a suture, includes inserting the suture receptacle end of the needle into a die which surrounds the needle at the receptacle end and inserting a suture into the suture receptacle. The needle is then indented in the area of the suture receptacle, forming a first indentation at a first longitudinal position and a first radial orientation. The needle is also indented in the area of the suture receptacle to form a second indentation at a second longitudinal position and a second radial orientation. The first and second indentations are longitudinally and radially offset and deform the suture at at least some portion of its length to approximate a reverse curve.

An armed suture made in accordance with the present invention has a needle with a suture receptacle at one end and a suture retained in the suture receptacle by a plurality of indentations in the needle wall disposed around the suture receptacle. The plurality of indentations include a first indentation in the needle wall and a second indentation in the needle wall longitudinally and radially offset from all other indentations of said plurality of indentations.

DETAILED DESCRIPTION OF THE INVENTION

Figure 1:
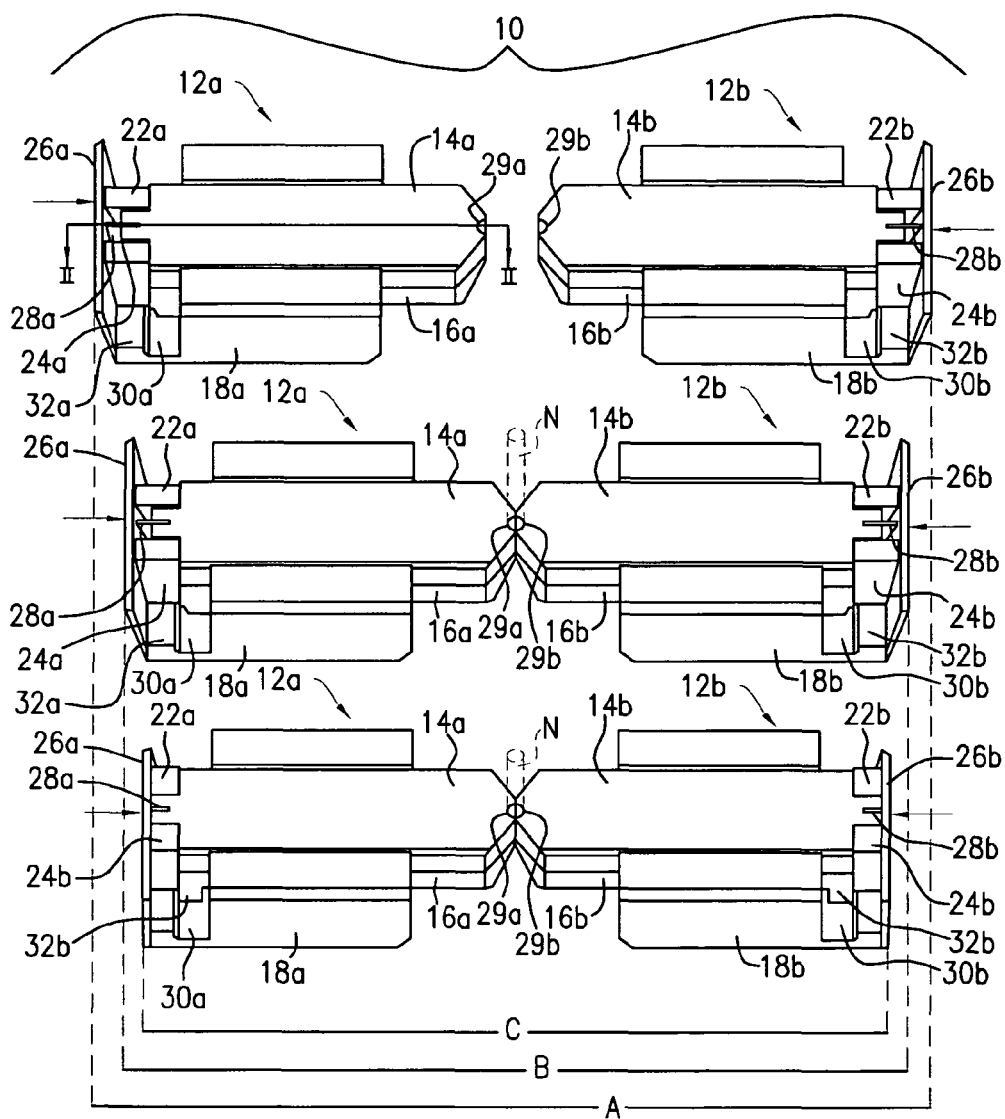
FIG. 1 is a perspective view of a pair of opposed swaging dies in accordance with an embodiment of the present invention in three stages of use.

FIG. 1 shows a needle swaging assembly 10 having first and second swage dies 12a, 12b in three different states of compression A, B, and C. Each of the swage dies 12a, 12b have a substantially identical structure, such that only the swage die 12a on the left hand side of FIG. 1 will be described. The reference numbering convention used, viz., reference numbers for identical elements of the two swage dies are the same except for a different subscript letter, indicates this commonality in structure and function. The present invention does not require identical or mirror-image swage dies 12a, 12b, however. Swage die 12a has a needle holder 14a and a needle stop 16a, which, when acting is conjunction with the corresponding parts 14b, 16b of swage die 12b, retain and support a needle N (a fragment of which is shown in phantom) to be attached to a suture by swaging. Both the needle holder 14a and the needle stop 16a are carried by a die support 18a which is attached to a conventional tool holder assembly of a swaging machine (not shown). Swaging machines conventionally utilize a mechanism, such as a cam or a hydraulic or pneumatic ram/cylinder acting either directly or through a lever arm to urge opposing dies towards one another for the purpose of impinging upon a needle to be swaged. The support 18a could therefore be adapted to be held by a tool holder of known swaging apparatus using techniques known to one normally skilled in the art. The swaging machine will have at least one surface that articulates relative to another surface, which may be stationary or articulating to conduct swaging. In the present application, pressure plates 26a, 26b which represent surfaces of the swaging machine that converge forcefully to actuate the swaging assembly 10. Swaging die 12a has a pair of springs or resilient blocks of elastomeric material 22a and 24a which urge the needle holder 14a and the pressure plate 26a apart and allow a swaging element 28a to assume a retracted position. The pressure plate 26a, may overcome the force exerted by the springs 22a, 24a to act upon stake 28a which extends through the interior of the needle guide 14a to impinge on the needle N during swaging, as shall be further described below.

In FIG. 1, the swage dies 12a, 12b are shown oriented in the horizontal direction, but could equally well be oriented vertically or in any other orientation, as long as they are opposed to one another and their respective movement is approximately along the same axis, such that they converge when compressed and diverge when uncompressed. Each of the needle holders 14a, 14b has a semi-cylindrical groove 29a, 29b for holding a needle therebetween when the dies 12a, 12b are urged together, the grooves 29a, 29b when conjoined, approximating a cylinder. The needle stop 16a has a limited range of freedom of motion along the axis of swage die movement relative to support 18a, which is delimited by the clearance between a keyway 30a in the support 18a and a mating key 32a projecting downwardly from the needle stop 16a, which is received in keyway 30a. The clearance permits the needle stop 16a to "float" relative to die support 18a allowing the needle holders 14a, 14b to assume positions: (i) to allow insertion of a needle therebetween, (ii) to support the needle during swaging and (iii) to permit removal of the needle after swaging. As shall be seen below, the needle guide 14a is fixedly keyed or otherwise mechanically conjoined, e.g., by threaded fasteners, to the needle stop 16a to prevent relative movement therebetween. FIG. 1 shows three positions A, B and C for the first and second swage dies 12a, 12b. In the first position, swage dies 12a, 12b are separated and the springs 22a, 24a, 22b, 24b are expanded, such that driven ends 40a, 40b (FIG. 2) of the swaging elements 28a, 28b extend beyond the rear surfaces of the needle holders 14a, 14b. In the second position B, the swaging machine has exerted an inward compressive force on the swage dies 12a, 12b (via pressure plates 26a, 26b) pushing them towards each other, such that the semi-cylindrical needle grooves 29a, 29b are brought into contact to form a cylinder for grasping a needle N. In position B, the springs, e.g., 22a, 22b, are still expanded. In position C, the swaging machine has exerted pressure via pressure plates 26a, 26b to compress the springs 22a, 24a, 22b, 24b and to urge the swaging elements 28a, 28b inwardly towards the needle N held in the semi-cylindrical needle grooves 29a, 29b.

Figure 2:
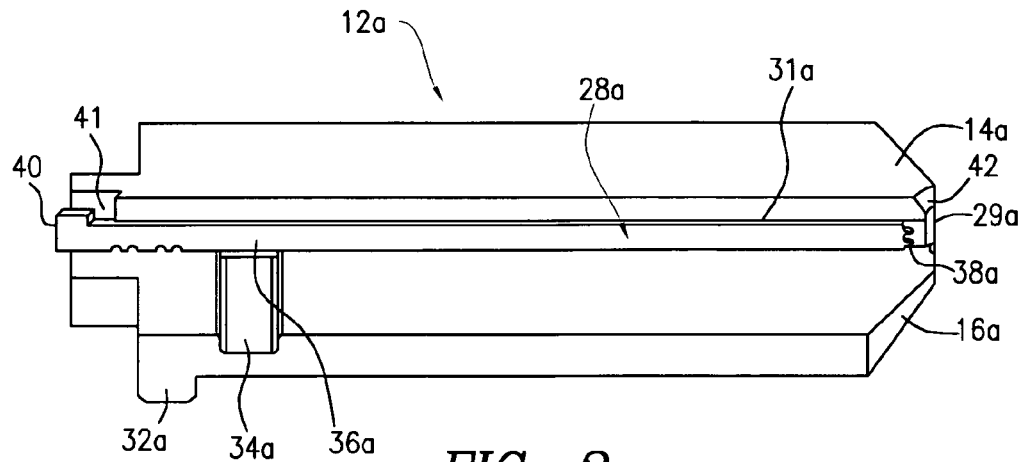
FIG. 2 is a cross-sectional view of one of the swaging dies of FIG. 1 taken along section line II-II and looking in the direction of the arrows.

FIG. 2 shows a cross-sectional view of swage die 12a wherein the swaging element 28a is visible in a slot 31a formed in the needle holder 14a. The driven end 40 of the swaging element 28a is enlarged and is received in corresponding keyway 41a, which limits its movement in the forward direction. As described above, the needle stop 16a has a key way 34a for receiving a key 36a extending from the bottom surface of the needle guide 14a. (The key 36a is just visible behind the swaging element 28a.) Key 32a extends from the bottom of the needle stop 16a. The swaging element 28a has a pair of points or stakes 38a which are driven into the needle to be swaged. In FIG. 2, the swaging element 28a is in the retracted position, such that the stakes 38a do not extend into the semi-cylindrical needle groove 29a. When in the extended position, the stakes 38a intrude into the groove 29a. Needle funnel portion 42a conjoins with a corresponding needle funnel portion 42b to form a conical taper that facilitates the insertion of a needle into conjoined abutting needle grooves 29a, 29b, which form a cylindrical receptacle for the needle N.

Figure 3:
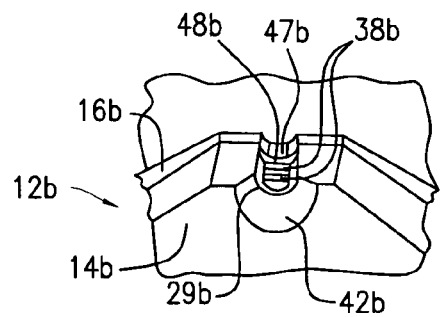
FIG. 3 is a perspective view of an end of one of the swaging dies of FIGS. 1 and 2.

FIG. 3 shows the end of swage die 12b with its semi-cylindrical needle groove 29b and needle funnel portion 42b. The needle stop 16b has a V-shaped suture groove 47b which guides the suture S into a suture receptacle SR in the needle N. Since the suture groove 47b has different dimensions than the semi-cylindrical needle groove 29b, a ledge 48b is formed relative to the needle groove 29b, against which the end of the needle N abuts, delimiting the position of the needle N when it is held in the dies 12a, 12b. When conjoined, the swage dies 12a, 12b hold the needle N and the suture S in alignment to permit the insertion of the suture S into the suture receptacle SR of the needle N.

Figure 4:
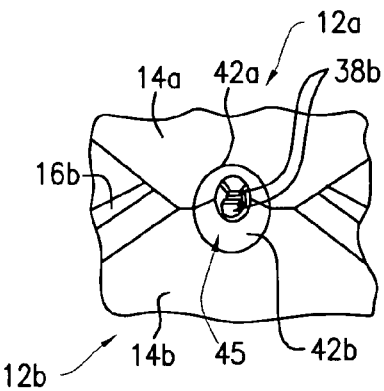
FIGS. 4 and 5 are perspective views of the swage dies of FIGS. 1-3 abutted and with the stake swage extended and retracted, respectively.
Figure 5:
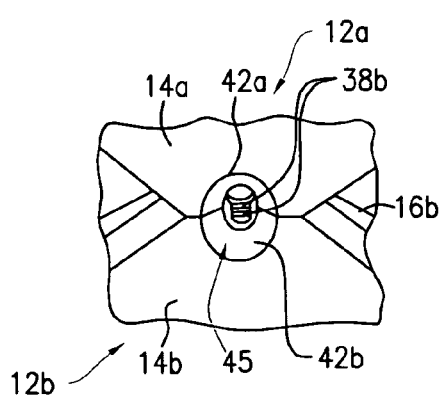

FIG. 4 illustrates the abutment of the first and second swage dies 12a, 12b whereby the semi-cylindrical needle grooves 29a, 29b of the needle holders 14a, 14b conjoin to form a substantially cylindrical receptacle 45 for receiving a needle N. The stakes 38b of the swaging elements 28b are visible through the cylindrical receptacle 45 between the swage dies 12a, 12b. In FIG. 4, the stakes 38b are extended into the cylindrical receptacle 45, whereas in FIG. 5, the swaging elements 28b and the stakes 38b are in the retracted position.

Figure 6A:
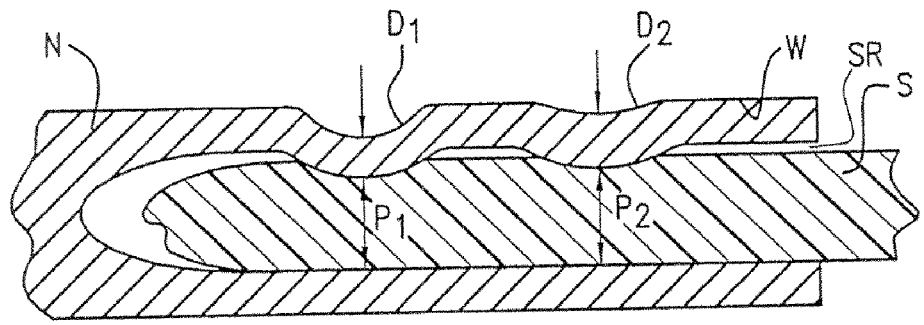
FIG. 6 is a cross-sectional view of an armed suture where the needle is attached to the suture by aligned, opposed stake swaging and by single stake swaging.
Figure 6B:
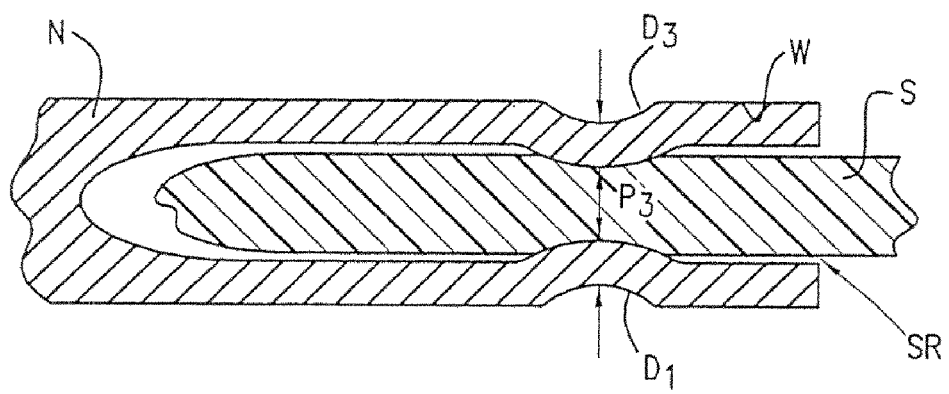

FIGS. 6a and 6b illustrate two prior art methods of swaging, namely single-sided, multiple indentation swaging (FIG. 6a) and double-sided, aligned swaging (FIG. 6b), which retain a suture S within a suture receptacle SR of a needle N. In single-sided swaging, the suture S is inserted into the suture receptacle SR of the needle N, and at least one stake point is driven into one side of the needle N in the suture receptacle SR region, deforming the wall W and creating a depression $D_1$. The depression $D_1$ causes the wall W of the needle N to impinge upon the suture S within the needle receptacle, creating a pressure point $P_1$ between the depression $D_1$ and the opposing portion for the needle wall W. One or more additional indentations $D_2$ can be made to create additional pressure points, e.g. $P_2$. As an alternative, if two opposed stakes are utilized, the points of which are aligned opposite to one another, two depressions $D_3$ and $D_4$ are made in the wall W of the needle N, creating a pressure point $P_3$ between the two depressions $D_3$, $D_4$. In either case, the suture is retained in the needle by virtue of the impingement of a small portion of the needle wall W on a correspondingly limited area of the suture S. As a result, the shear force exerted at pressure points $P_1$, $P_2$ or $P_3$ is focused on a very limited area of the suture S. In order to create sufficient holding force, depressions $D_1$, $D_2$, $D_3$, $D_4$ must protrude inwardly to an extent that grasps the suture S with sufficient force. The focused pressure at $P_1$, $P_2$, $P_3$ creates shear stress which may result in fracturing of the suture, leading to suture detachment. To avoid exceeding the shear stress limits of the suture material, the dimensions of the suture receptacle SR, the thickness and deformability (material dependent) of the wall W, the depression depth of depressions, e.g., $D_1$, (all degrees of precision that are difficult and expensive to achieve and maintain), must be carefully controlled.

Figure 7:
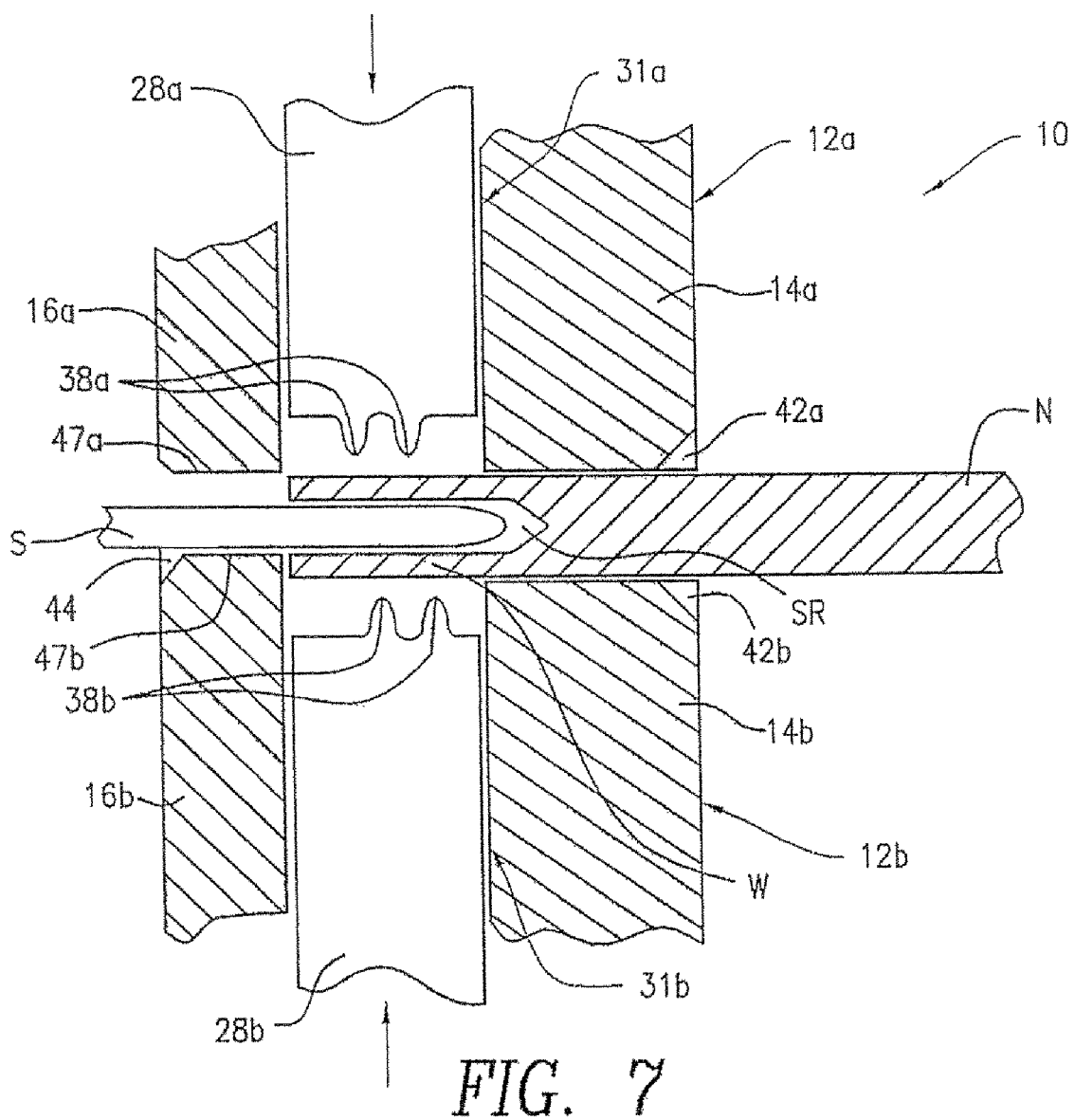
FIG. 7 is a cross-sectional view of a needle held in the swage die of FIGS. 1-5.

FIG. 7 shows the needle swaging assembly 10 with first and second swage dies 12a, 12b converging to hold a needle N for swaging. The needle N is gripped between needle holders 14a, 14b and abuts against needle stops 16a, 16b with the suture receptacle SR aligned with the suture grooves 47a, 47b. Insertion of the needle N between the needle holders 14a, 14b is facilitated by needle funnel portions 42a, 42b. The suture funnel 44 aids in threading the suture S through the suture grooves 47a, 47b and into the suture receptacle SR. Swaging elements 28a, 28b are slideably received in and articulate in corresponding slots 31a, 31b such that the stakes 38a, 38b thereof, respectively, can impinge upon the needle N. In FIG. 7, the swaging elements 28a, 28b both feature a plurality of stakes 38a, 38b; The stakes 38a are laterally offset relative to the stakes 38b such that when the swaging elements 28a, 28b are urged together during the swaging operation, the needle N will be swaged to create a serpentine configuration in the suture receptacle SR. A greater or lesser number of stakes 38a, 38b may be utilized, ranging from one stake 38a, 38b on each swaging element 28a, 28b, up to any selected number of stakes 38a, 38b. The height, spacing and shape of the stakes 38a, 38b, as well as the relative lateral offset of stakes 38a, 38b on opposing swaging elements 28a, 28b, may be selected to adjust swaging and suture attachment strength.

Figure 8:
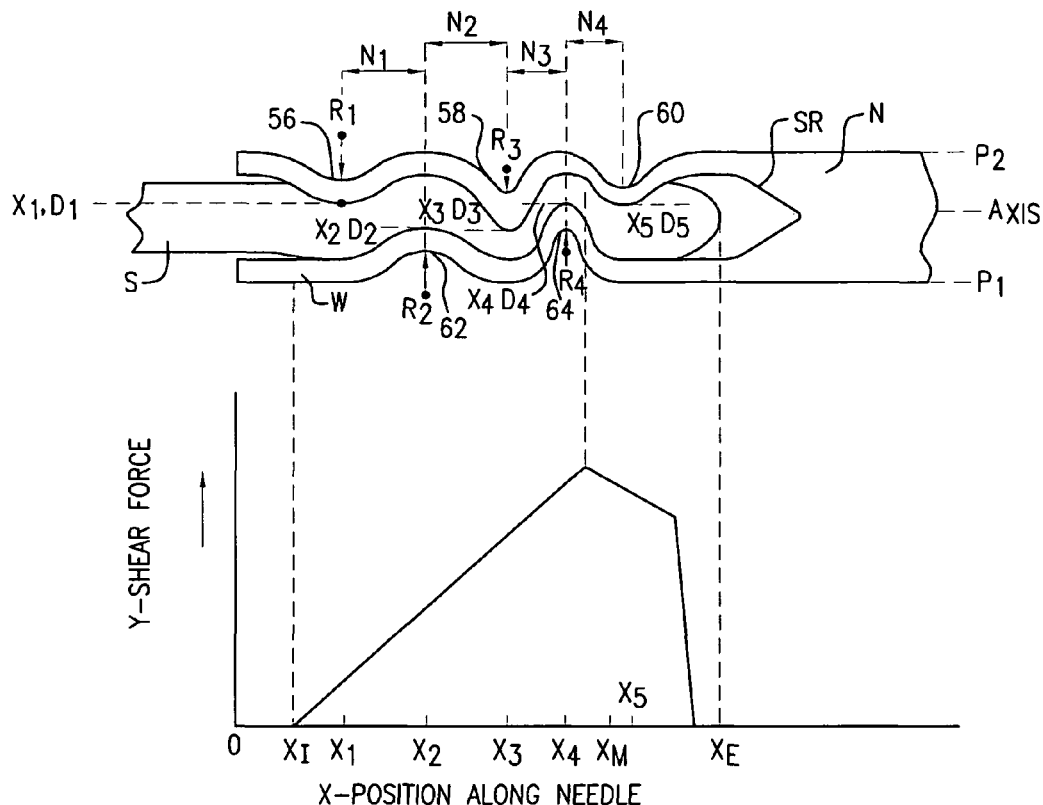
FIG. 8 is a cross-sectional view of a needle that has been swaged in accordance with the present invention.

FIG. 8 shows the generally S-shaped or serpentine configuration of the suture receptacle SR and enclosed suture S resulting from offset swaging conducted in accordance with the present invention. The sheer force experienced by the suture S at any given point X along the suture-needle interface is graphically illustrated. As can be seen by the graph in the lower portion of FIG. 8, the shear force increases from left to right starting at $X_P$, to a maximum at $X_M$ and then drops off at the end $X_E$ of the suture S within the suture receptacle SR. This illustrates a recognition of the present invention that the shear force can be affected, distributed and controlled by a number of factors, namely the depth of the indentation made by the stakes, e.g. 28a, the radius of curvature of the stakes, and the relative spacing of the stakes. For example, indentations 56 and 62 have radii of curvature $R_1$, $R_2$ respectively, which are approximately equal, as are the depth of penetration of the depressions 56, 62, viz., $D_1$ and $D_2$, respectively. (The depth of penetration can be expressed relative to the central axis of the needle and/or the outer peripheral surfaces $P_1$, $P_2$.) The distance between depressions, N1, N2, etc. in conjunction with the radius of curvature, depression depth and relative lateral offset are adjustable parameters that may be varied to achieve desired shear and frictional forces. In general, lesser indentation depths, larger radiuses, wider spacing between depressions and peak-to-valley relative lateral offset result in more even distribution of shear forces along the length of the swaged suture-needle interface hence, lower maximum shear force values. Accordingly, greater indentation depths, smaller radiuses, narrower spacing between depressions and peak-to-peak lateral alignment result in greater concentration of shear force at the suture-needle interface. The present invention recognizes that each of these parameters may be varied to control shear force distribution and that such variations along the length of the needle-suture interface and further, gradually increasing shear force with increasing depth into the suture receptacle results in easier, more reliable suture attachment. For example, in FIG. 8, $R_1$ and $R_2$ are approximately equal, but $D_2$ is greater than $D_1$ resulting in an increase in shear force. The distance $N_2$ is approximately equal to the distance $N_1$, however radius $R_3$ associated with indentation 58 is less than $R_1$ or $R_2$ and the depth of penetration $D_3$ is greater, causing a more severe/focused intrusion into the suture receptacle SR and an increase in shear force. Indentation 64 has an even smaller radius of curvature $R_4$ and a greater depth of penetration $D_4$ leading to an even greater shear force.

In FIG. 8, the indentations 62, 64 are laterally offset relative to indentations 56, 58, 60 such that there is peak-to-valley relative alignment. This is consistent with one of the basic teachings of the present invention, viz., peak-to-valley relative alignment results in greater contact area between needle N and suture S (and hence greater frictional interaction and more even distribution of shear force resulting in greater cumulative force over a greater contact area (suture-needle interface) than peak-to-peak alignment. Moreover, a tortuous, serpentine suture-needle interface requires the entire length of effected suture (in the swaged area) to simultaneously rebend to conform to the serpentine shape under the influence of its frictional interaction with the interior surface of the deformed suture receptacle in order to be pulled from the suture receptacle SR. This contrasts with pulling an otherwise unconstrained suture from a pinch point between two opposed indentation peaks. As can be appreciated, the suture receptacle is deformed by swaging into a converging serpentine space. The present invention recognizes that it is beneficial to gradually increase the shear force area with increasing depth into the suture receptacle SR for two reasons, viz., (1) the increased shear force results in greater surface-to-needle contact and increased frictional interaction between suture and needle; (2) unlike peak-to-peak swaging, the swaged area giving rise to the excessive shear force is not the only area of suture-needle attachment. In the present invention, because the swaged area gradually converges with greater depth into the suture receptacle, the area of greatest sheer force may be exerted deep within the suture receptacle SR such that, even if the maximum sheer force is exceeded at a position far into the suture receptacle, pinching of the suture will not result in suture separation from the needle, in that the swaged areas in shallower regions of the suture receptacle SR are adequate to maintain suture-needle attachment.

Figure 9:
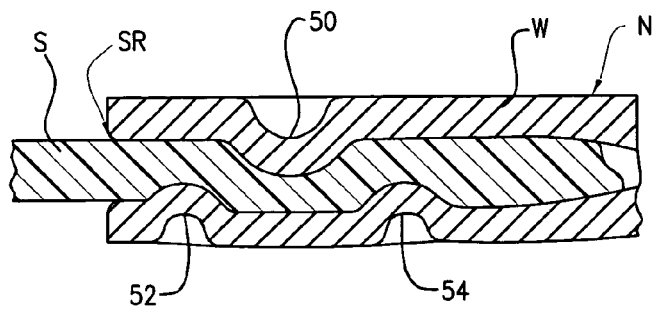
FIG. 9 is a cross-sectional view of an armed suture where the needle is attached to the suture by offset stake swaging in accordance with the present invention.
Figure 10:
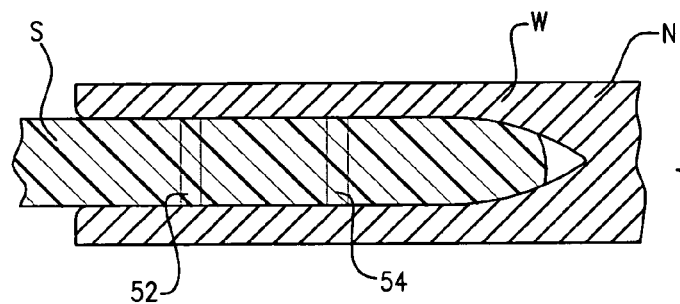
FIG. 10 is a cross-sectional view of the armed suture of FIG. 7 taken at an orientation substantially perpendicular to that of FIG. 7.
Figure 11:
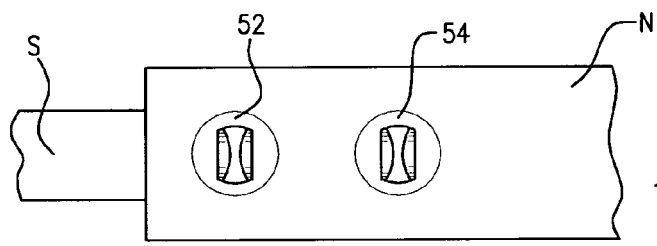
FIG. 11 is a side view of a needle that has been staked in accordance with an embodiment of the present invention.

FIGS. 9-11 illustrate an armed suture made in accordance with the present invention. More particularly, FIG. 9 shows a needle, N having a plurality of swaged indentations 50, 52 and 54 which result in a serpentine suture receptacle SR for grasping the suture S. The indentations were formed by utilizing a first stake with stake points, e.g., 38a, 38b that are spaced apart yielding depressions 52, 54 that are spaced along the length of the needle in the suture receptacle area. On the opposite side of the needle, a stake with a single stake point was impinged on the needle to create a depression 50 in the wall W of the needle intermediate depressions 52, 54, i.e. in peak-to-valley alignment. FIG. 10 is a cross section of the needle of FIG. 9 taken at 90° relative to the view shown in FIG. 9. The tops of the indentations 52, 54 are visible through the suture S which is translucent, the indentation 50 having been removed in this cross-sectional view. FIG. 10 shows how a suture S may be deformed by swaging to radially fill the suture receptacle SR in an even manner, whereby the frictional interaction between the suture receptacle SR and the suture S is enhanced. FIG. 11 shows the exterior of the needle end with the suture S extending therefrom and with the two depressions 52, 54 extending into the wall W of the needle N.

Figure 12:
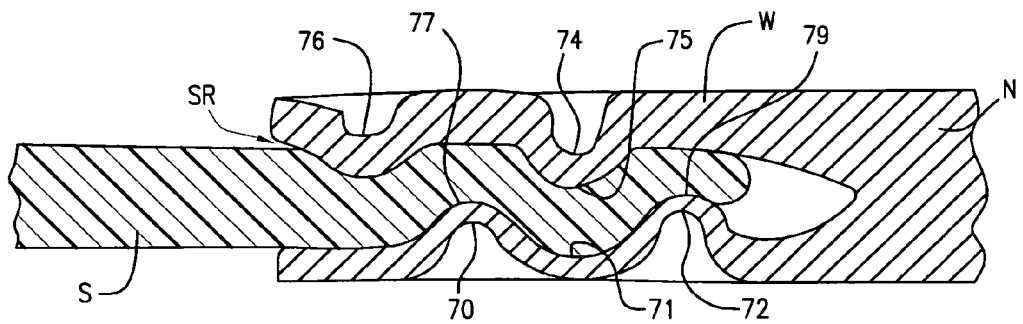
FIG. 12 is a cross-sectional view of an armed suture where the needle is attached to the suture by offset stake swaging in accordance with the present invention.

FIG. 12 shows a suture S retained in suture receptacle SR of needle N. The needle has four alternating indentations 70, 72, 74, 76 made in the wall W of the needle N. The indentations are in peak-to-valley alignment, viz., the peak 75 made by indentation 74 is aligned with the valley 71 between the peaks 77 and 79 associated with depression 70 and 72, respectively.

Figure 13:
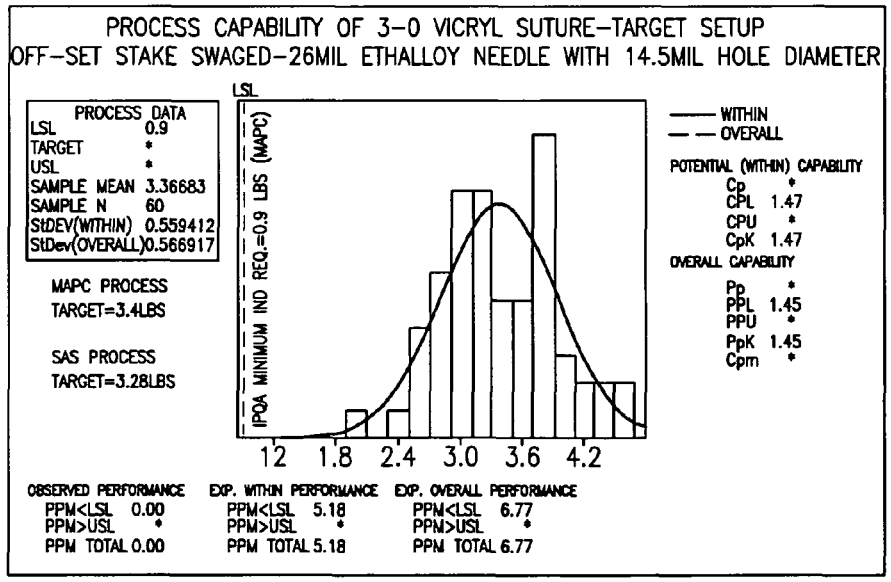
FIG. 13-17 are graphs of pull strength performance for five different sets of armed suture samples made in accordance with the present invention, with FIG. 15 also illustrating comparative results produced by another swaging method.

FIG. 13 shows the process capability of the automated attachment of 3/0 Vicryl suture to laser drilled 26 mil. needles with a suture receptacle having a diameter of 14.5 mils. This diameter was chosen to be in excess of the standard hole size used for producing armed sutures of this type commercially by square swaging methods. More specifically, the established process requires a suture receptacle having a diameter of 12.8 mils to provide adequate pull strength, but has wastage implications due to a significant percentage of failures of the suture to insert into the suture receptacle and "hook-up" or attach after swaging—as determined by pull testing to a limit of 0.9 lbs. Increasing the size of the suture receptacle to 14.5 mils. therefore significantly increases the likelihood of successful suture insertion into the suture receptacle. However, using known swaging methods, such as square swaging, the increase in suture receptacle size would have negative implications on successful needle-suture attachment. A swaging method and apparatus as described above (four stake point, opposed, offset swage staking, e.g., as illustrated in FIG. 7) and in accordance with the present invention was utilized to swage the needles with the oversized suture receptacles and the results graphed in FIG. 13 were realized. More particularly, given a sample size of 60, a sample mean pull strength of 3.36 lbs. pull strength before separation was achieved, which greatly exceeded the lower spec limit of 0.9 lbs. pull strength. There were no suture attachment failures nor any pull strengths less than the minimum of 0.9 lbs observed.

Figure 14:
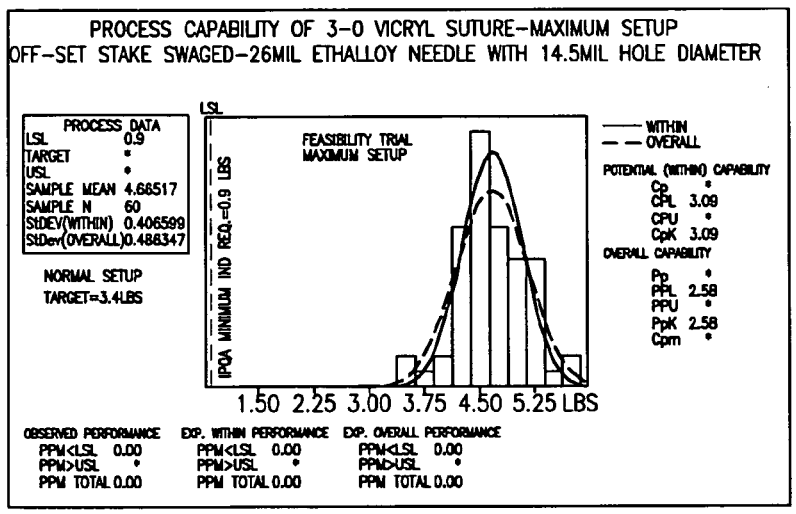

The graph shown in FIG. 14 illustrates the results obtained with a second sample set of 60 armed sutures, where the swaging (indentation) depth was increased above that utilized in making the sample set of FIG. 13. While still below the pinch-off threshold of excessive shear force, the mean pull strength increased to 4.66 with no failures to attach or clip-offs observed and a short term IPQA Cpk of 3.1.

Figure 15:
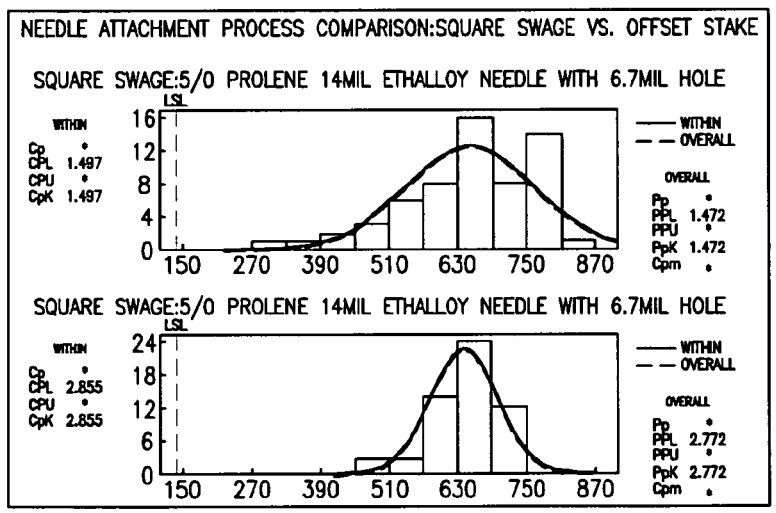

FIG. 15 shows two histograms of attachment strength for the same needle/suture combination, viz., 5/0 Prolene suture swaged to a 14 mil. needle with a 6.7 mil. hole but using different swaging techniques. At the top, square swaging results in an overall PPL and Ppk of 1.472. The bottom histogram shows improvement in needle attachment, with a PPL and Ppk of 2.772, indicating an excellent process.

Figure 16:
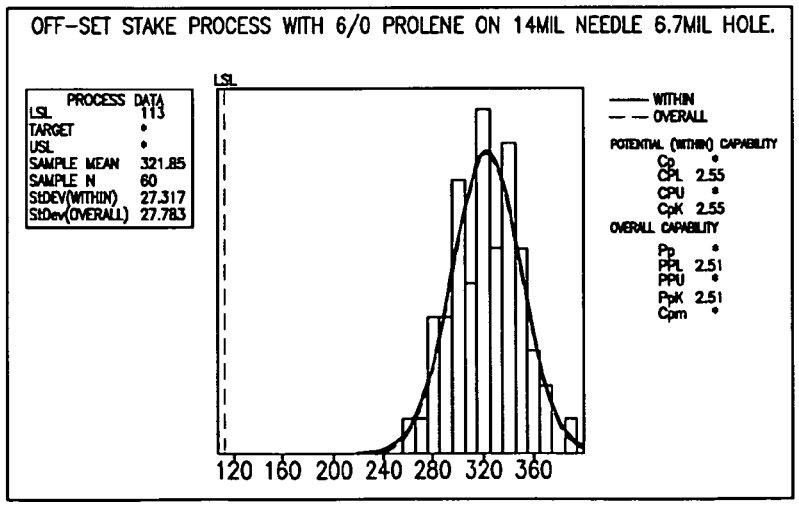
Figure 17:
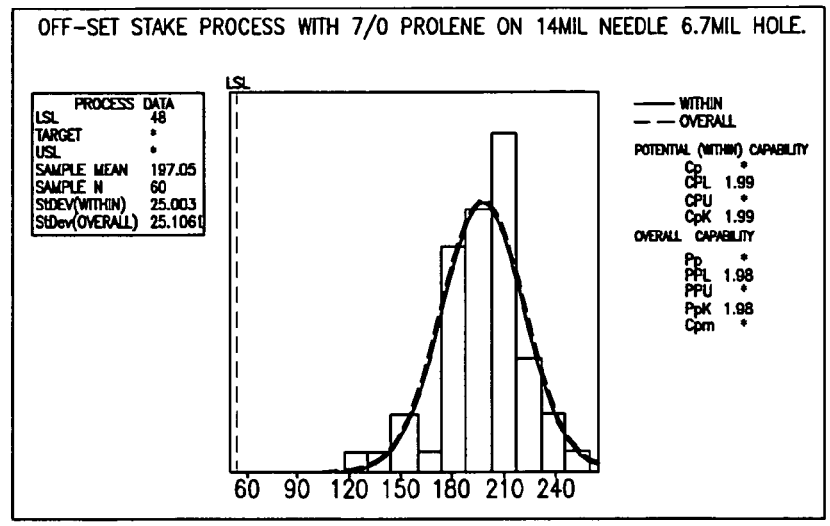

FIGS. 16 and 17 show pull strength results for the same needle and off-set swaging process used to generate the results shown in the bottom of FIG. 14, but using 6/0 and 7/0 sutures respectively. The use of thinner sutures result in PPL and Ppk values of 2.51 and 1.98, respectively, and mean pull strengths that are far in excess of the lower spec limit. These results illustrate that a swaging apparatus made in accordance with the present invention can be used to swage a range of different sized sutures to a given needle with results exceeding those accomplished by traditional methods.

Figure 18:
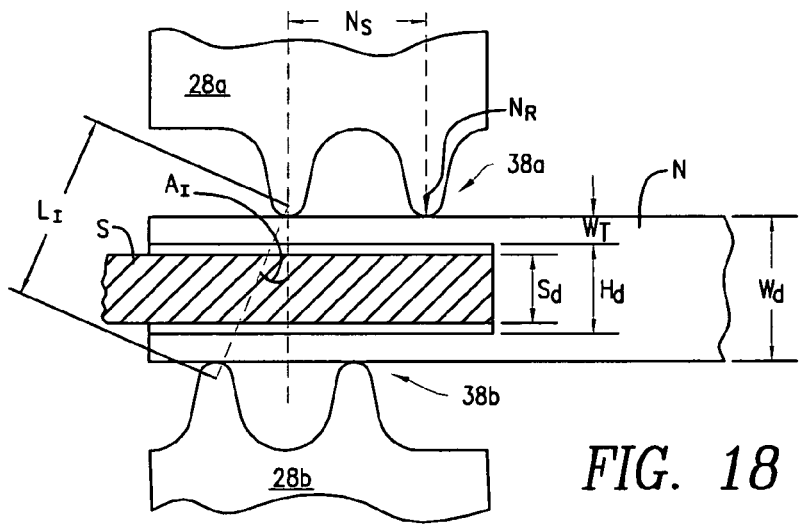
FIGS. 18 and 19 are diagrams illustrating certain dimensions of swaging stakes and the resultant indentations in a needle barrel formed thereby which may be used to quantify and predict suture compression and shear force.
Figure 19:
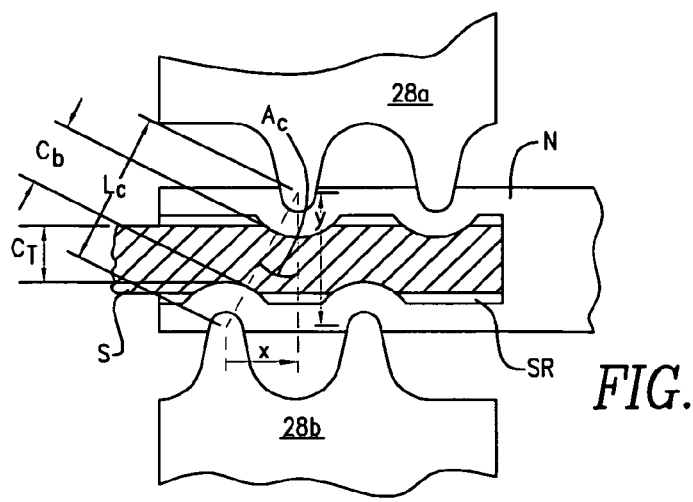

FIGS. 18 and 19, illustrate various dimensions of the suture, needle, stakes and relative positions thereof that may be used to calculate the spacing between stakes to achieve a specific suture compression ratio and to illustrate generally the relationships between the relevant dimensions and suture compression ratio. More specifically, the following variable names will be used:

| Variable Names | |
|---|---|
| Wire (needle) diameter - $W_d$ | Suture compression ratio over nib (stake) - $C_T$ |
| Suture diameter - $S_d$ | Suture compression ratio between opposed, neighboring nibs (stakes) - $C_b$ |
| Hole diameter - $H_d$ | Ratio of $C_b/C_T$ - Ratio |
| Nib (stake) radius - $N_R$ | Angle between centerlines of neighboring, opposed nibs at compression - $A_C$ |
| Initial length, centerline-to-centerline between neighboring opposed nibs (before compression) - $L_I$ | Angle between centerlines of neighboring, opposed nibs (before compression) - $A_I$ |
| Wall thickness - $W_T$ | Lateral (x-direction) spacing between nibs - $N_S$ |
| Suture compression ratio - C | Length between centerlines of opposed, adjacent nibs in compressed state - $L_C$ |

The following equations describe certain relationships between the foregoing variables.

Relationships

Wall Thickness
$$W_T := \frac{W_d - H_d}{2}$$

Compression over nib $\quad C_T := S_d * (1 - C)$
Compression between nibs $\quad C_b := \text{Ratio} \cdot C_T$
$N_s := ((2 \cdot N_R + 2 \cdot W_T + \text{Ratio} \cdot C_T)^2 - [2 \cdot N_R + 2 \cdot W_T + 2 \cdot (S_d/2 - S_d + C_T)]^2)^{1/2}$
$A_I := \text{atan}(N_S/W_d + 2N_R)$
$L_I := [N_s^2 + (W_d + 2N_R)^2]^{1/2}$
$A_C := \text{atan}[N_S/(W_d + 2N_R - 2(H_d - S_d + C \cdot S_d))]$
$L_C := [N_s^2 + (W_d + 2N_R - 2(H_d - S_d + C \cdot S_d))^2]^{1/2}$
$C_b := L_c - 2N_R - 2[(W_d - H_d)/2]$ The following are examples to illustrate the use of the foregoing relationships to calculate selected values.

Example 1

Given:
Wire Dia $W_d := 0.026$
Suture Dia $S_d := 0.01255$
Hole Dia $H_d := 0.0157$
Nib Radius $N_R := 0.003$
Suture Compression Ratio C:=10%; then
Nib Spacing $N_s := 0.012''$
$C_b := 0.0098''$
$C_T := 0.0113''$
Ratio:=0.8686
$A_c := 27.36°$

Example 2

Given:
Wire Dia $W_d := 0.026''$
Suture Dia $S_d := 0.01255''$
Hole Dia $H_d := 0.0157''$
Nib Radius $N_R := 0.003''$
Suture Compression Ratio C:=20%; then
Nib Spacing $N_s := 0.012''$
$C_b := 0.0076''$
$C_T := 0.0100''$
Ratio:=0.760
$A_c := 30.125°$

Example 3

Figure 20:
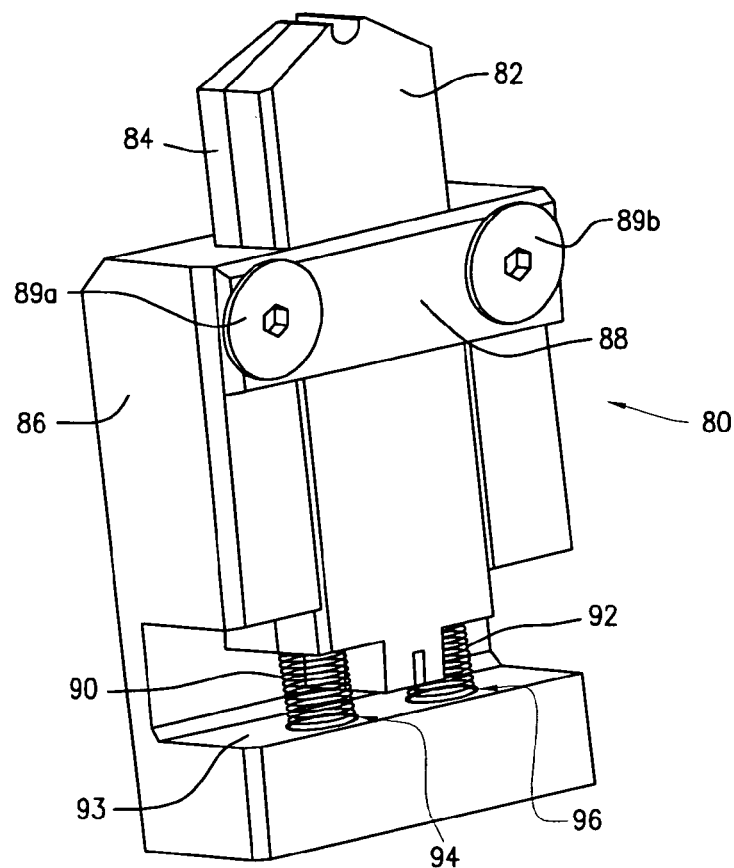
FIG. 20 is a perspective view of a swaging die in accordance with an alternative embodiment of the present invention.

Wire Dia $W_d := 0.026$
Suture Dia $S_d := 0.01255$
Hole Dia $H_d := 0.0157$
Nib Radius $N_R := 0.003$
Suture Compression Ratio C:=26%; then
Nib Spacing $N_s := 0.012''$
$C_b := 0.0063''$
$C_T := 0.0092''$
Ratio:=0.6804
$A_C := 32.04°$ FIG. 20 shows another type of swage die 80 having a needle guide 82 and needle stop 84 similar to that shown in FIGS. 1-5, but held in a support 86 by a cap 88 retained to the support 86 by a pair of Allen bolts 89a, 89b or the like. The needle guide 82 and needle stop 84 are urged away from a ledge 93 of the support 86 by a pair of springs 90, 92, e.g., coil springs. The springs may be inserted into corresponding sockets 94, 96 to prevent them from slipping out of position on the ledge 93. Similar sockets or other spring retaining means (not shown) may be provided on the needle guide 82 and/or the needle stop 84 to retain the springs 90, 92.

Figure 21:
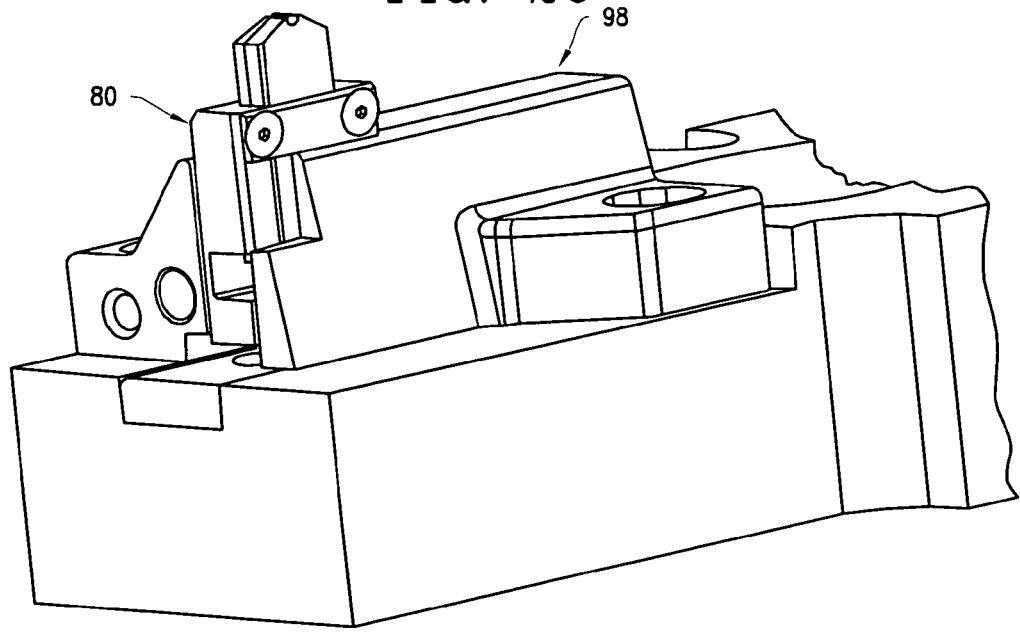
FIG. 21 is a perspective view of a die holder holding the swage die of FIG. 20.

FIG. 21 shows the swage die 80 of FIG. 20 held in a needle holder 98.

The present invention, by diminishing the levels of required precision and increasing the tolerances of production, diminishes wastage due to ineffective attachment procedures and increases quality of needle-to-suture attachment. By decreasing the criticality of manufacturing tolerances, it permits use of a common, single hit swaging process and apparatus to attach different types of needles and sutures, e.g., laser, EDM or mechanically drilled needles, fabricated from one or more of a variety of different alloys including ETHAL-LOY® 4310, 455, and 420 alloys (sold by Ethicon, Inc.), which may be annealed or non-annealed, to various types of sutures, such as braided, twisted, or monofilament sutures made from synthetic or natural materials. By utilizing a die which constrains the needle, 'bell-mouth' or 'fin' formation defects are eliminated and needle barrel outside diameter remains substantially uniform across the attachment region. The increased tolerances utilized in the set-up and use of the swaging apparatus of the present invention allows operators of every experience level to set-up batches quicker and more consistently when using the same swage die series for all attachment work. The increased tolerance also allow one set of dies to be used on a range of different suture sizes and suture receptacle diameters, eliminating a corresponding multiplicity of more specialized dies.

We claim:

1. A swaging apparatus driven by a swaging machine with a pair of actuating surfaces that selectively converge to exert pressure and diverge to release pressure on the swaging apparatus for attaching a needle to a suture, the needle having a suture receptacle at one end for receiving the suture, which is retained therein by swaging the needle in the area of the suture receptacle, comprising: (A) a die assembly with a needle aperture therein, said needle aperture receiving the needle therein, said die assembly having a plurality of swage passageways therein communicating with the needle aperture and extending through the die assembly at a plurality of radial orientations relative to the needle aperture, and (B) a plurality of swaging elements each of which are insertable into corresponding ones of said plurality of swage passageways, each of said swaging elements having an end with at least one stake, at least one of said stakes on a first swaging element being laterally offset relative to said stakes on the remainder of said plurality of swaging elements.

2. The swaging apparatus of claim 1, wherein the needle aperture confines a portion of the needle during swaging to substantially limit the deformation of the needle during actuation of the swaging elements.

3. The swaging apparatus of claim 2, wherein said swaging apparatus includes a pair of dies, each having a needle groove, said pair of dies conjoinable with said needle grooves aligned to define said needle aperture, each die of said pair of dies having at least one of said swage passageways therein accommodating at least one of said swaging elements.

4. The swaging apparatus of claim 3, wherein each said die has a needle holder portion in which said needle groove is formed and a needle stop portion, at least one of said needle stop portions having a suture groove formed in an end thereof, said at least one needle stop portion coupled to said needle holder portion with said suture groove positioned proximate said needle groove, said needle stops of said pair of dies conjoinable to form a suture passageway and a ledge against which the needle abuts when fully inserted into the needle aperture, said suture passageway and said needle aperture being aligned to permit the suture to be threaded into the suture receptacle when said needle is held in said swaging apparatus.

5. The swaging assembly of claim 4, wherein said needle holder and said needle stop of each die of said pair of dies are coupled to prevent relative motion therebetween.

6. The swaging apparatus of claim 5, wherein each of said swaging elements has a length in excess of the length of a corresponding needle holder in which it is received, each of said plurality of swaging elements having a retracted position wherein said at least one stake is withdrawn into said swaging passageway such that it does not extend into the needle groove and a driven end thereof extends out of the needle holder distal to the needle groove and an extended position wherein said at least one stake extends into said needle groove.

7. The swaging apparatus of claim 6, wherein each of said dies has at least one resilient member urging the needle holder away from an associated actuating surface of the swaging machine, said resilient member being expanded when the actuating surfaces are diverged and compressed when the actuating surfaces are converged, the actuating surfaces bearing upon and pushing respective said swaging elements through corresponding said swaging passageways and driving said stakes thereof into the needle aperture of the needle guide and into a needle held therein.

8. The swaging apparatus of claim 7, wherein each of said pair of dies is held in a die support having a die channel, said die support slideably embracing the coupled needle stop and needle holder within said channel, said needle stop being constrained to a limited range of sliding motion within said channel extending from an open position permitting insertion of the needle into said needle aperture and a closed position in which the needle is held in the needle aperture under compressive force exerted by the actuating surfaces acting through the resilient members, and wherein each of said plurality of swaging elements has a stop which interacts with a corresponding said swaging passageway to control the extension of said at least one stake into said needle aperture.

* * * * *